(12) United States Patent
Andersen et al.

(10) Patent No.: US 8,003,842 B2
(45) Date of Patent: Aug. 23, 2011

(54) HYDROCARBON SEPARATION

(75) Inventors: Simon Ivar Andersen, Tikøb (DK); Annette Leerskov, Kastrup (DK); Peter Jakob Mune, Slagelse (DK)

(73) Assignee: Haldor Topsøe A/S, Lyngby (DK)

( * ) Notice: Subject to any disclaimer, the term of this patent is extended or adjusted under 35 U.S.C. 154(b) by 551 days.

(21) Appl. No.: 11/951,963

(22) Filed: Dec. 6, 2007

(65) Prior Publication Data

US 2008/0154084 A1  Jun. 26, 2008

Related U.S. Application Data

(63) Continuation-in-part of application No. 11/634,070, filed on Dec. 6, 2006, now Pat. No. 7,777,089.

(51) Int. Cl.
*C07C 7/12* (2006.01)

(52) U.S. Cl. .................. 585/820; 585/825; 585/828

(58) Field of Classification Search .............. None
See application file for complete search history.

(56) References Cited

U.S. PATENT DOCUMENTS

| | | | |
|---|---|---|---|
| 2,768,942 A | 10/1956 | Marple, Jr. et al. |
| 2,958,714 A | 11/1960 | Kearby |
| 4,956,521 A | 9/1990 | Volles |
| 5,565,066 A | 10/1996 | Marker et al. |
| 6,069,289 A | 5/2000 | Dandekar et al. |
| 6,353,144 B1 | 3/2002 | Ragil et al. |
| 7,037,422 B2 | 5/2006 | Maesen et al. |
| 2006/0065576 A1 | 3/2006 | Broutin et al. |

FOREIGN PATENT DOCUMENTS

| | | |
|---|---|---|
| EP | 0 934 996 A1 | 8/1999 |
| GB | 982445 | 2/1965 |
| WO | WO 94/17017 | 8/1994 |

OTHER PUBLICATIONS

H. Schulz et al., "Deactivation of HZSM5 Zeolite During Methanol Conversion: Kinetic Probing of Pore-Architecture and Acidic Properties", Catalyst Deactivation 1991, Elsevier Science Publishers B.V., Amsterdam, pp. 783-791.
E. J. Munson et al., "In Situ Solid-State NMR Study of Methanol-to-Gasoline Chemistry in Zeolite HSZSM-5", Journal of Physical Chemistry, 1992, vol. 96. No. 19, pp. 7740-7746.
J. Li et al., "Coke Formation During the Methanol Conversion to Olefins in Zeolites Studied by UV Raman Spectroscopy", Microporous and Mesoporous Materials, vol. 39, 2000, pp. 275-280.
C. Li et al., "Ultraviolet Raman Spectroscopy Characterization of Coke Formation in Zeolites", Catalysis Toda , vol. 33, 1997, pp. 353-360.

(Continued)

*Primary Examiner* — Tam M Nguyen
(74) *Attorney, Agent, or Firm* — Dickstein Shapiro LLP

(57) ABSTRACT

A process for the separation of close boiling compounds comprising distilling a hydrocarbon mixture of said compounds in the presence of a high boiling diluent liquid and a solid adsorbent. The high boiling diluent is withdrawn from the bottom of the distillation column and recycled to the column. The process is particularly suitable for the separation of straight-chain isomers from isomerate mixtures, the separation of benzene from hydrocarbon mixtures and the separation of paraffins from olefins.

4 Claims, 6 Drawing Sheets

OTHER PUBLICATIONS

S-J. Jong et al., "On the Regeneration of Coked H-ZSM-5 Catalysts", Journal of Catalysis, vol. 174, 1998, pp. 210-218, Article No. CA981971.

A.R. Pradhan et al., "EPR and NMR Studies of Coke Induced Selectivation Over H-ZSM-5 Zeolite During Ethylbenzene Disproportionation Reaction", Journal of Catalysis, vol. 184, 1999, pp. 29-38.

L-Y. Fang et al., "Enhanced *para*-Selectivity by Selective Coking During Toluene Disproportionation Over H-ZSM-5 Zeolite", Journal of Catalysis, vol. 185, 1999, pp. 33-42.

F. Bauer et al., "Reactivation of Coked H-ZSM-5 by Treatment with Hydrogen and Alkanes", Journal of Catalysis, vol. 164, 1996, pp. 146-151.

Gounaris et al., "Rational Design of Shape Selective Separation and Catalysis—I: Concepts and analysis" *Chemical Engineering Science* 61, 2006, pp. 7933-7948.

HYDROCARBON SEPARATION

This is a continuation-in-part of U.S. application Ser. No. 11/634,070, filed Dec. 6, 2006, now U.S. Pat. No. 7,777,089.

FIELD OF THE INVENTION

The present invention relates to a process and apparatus for the separation of compounds having similar boiling temperatures. In particular, the invention relates to the separation of compounds of similar boiling temperatures in hydrocarbon isomerates, more particularly to the separation of mono and/or multibranched alkanes and cyclic alkanes from normal alkanes in $C_7$ isomerate mixtures such as the separation of n-$C_7$ from methylcyclohexane (MCH). The invention relates also to the separation of aromatic compounds in hydrocarbon mixtures, such as the separation of benzene from other hydrocarbons, in particular the separation of benzene from toluene in naphta cuts. The invention relates also to the separation of paraffins from olefins, in particular the separation of propylene from propane in propane-propylene fractions.

BACKGROUND OF THE INVENTION

The efficient removal of low-octane-number straight chain isomers, i.e. normal alkanes, from isomer mixtures is an important step in the generation of mixtures of high octane number for use in gasoline pools as well as for the efficiency of catalytic isomerisation processes. A number of processes have been disclosed dealing with this issue, most of them related entirely to $C_5/C_6$ isomer blends. U.S. Pat. No. 4,956,521 discloses the use of different adsorber beds with different specific zeolites for the removal of n-alkanes and mono-branched alkanes from $C_5/C_6$ isomers.

U.S. Pat. No. 6,069,289 describes a process for separating multimethylbranched alkanes, which are compounds of high octane number from the effluent of an isomerisation reactor by using a single adsorbent in a moving bed and two desorbents of different desorption capacities. The adsorbent may be silicalite, ferrierite, zeolite Beta, MAPO-31, SAPO-31, SAPO-11, and zeolite X and zeolite Y ion exchanged with cations.

U.S. Pat. No. 6,353,144 describes a process for separating isomers from a $C_5$-$C_8$ isomer mixture by injecting the isomer mixture into a chromatographic separation zone containing a zeolite adsorbent alternately with an eluent that enables the different adsorbed compounds of the isomer mixture to be desorbed.

U.S. Pat. No. 7,037,422 discloses a process for separating the high-octane-number compound naphta from an isomer mixture of $C_5$ and $C_6$ alkanes by contacting the isomer mixture with a CFI zeolite. Branched isomers of $C_5$ and $C_6$ alkanes are adsorbed and subsequently desorbed. In the zeolite, $C_5$ and $C_6$ alkanes are isomerised to the high octane number compounds methylbutane and dimethylbutane, and since methylbutane and dimethylbutane have a lower boiling point than, respectively, the other $C_5$-isomers and $C_6$-isomers, they are recovered by catalytic distillation in the same column.

U.S. Pat. No. 5,210,333 describes the use of adsorption on NaX and NaY zeolites in a fixed bed combined with a hydrogenation functionality that saturates adsorbed aromatics.

SUMMARY OF THE INVENTION

We have now found that by diluting a hydrocarbon stream containing an isomerate mixture with a diluent solvent of higher boiling point, it is possible to separate close boiling isomeric hydrocarbons in a distillation column having an adsorbent arranged therein. In contrast with the processes of the prior art, we have surprisingly found that a distillation can be performed such that specific components can be retained in the column even if the boiling point is lower than the compounds distilling from the column. The other components boiling either higher or lower than the retained component(s) may be withdrawn as a distillate stream without carrying the diluent solvent.

Accordingly, we provide a process for the separation of isomers from an isomerate mixture comprising normal alkanes, mono-branched alkanes and multi-branched alkanes, the process comprising:
(a) passing said isomerate mixture to a distillation stage, said distillation stage comprising an adsorbent in an adsorption zone which is in contact with a diluent liquid solution having a boiling point which is higher than that of the isomerate mixture,
(b) withdrawing from said distillation stage a distillate stream containing mono-branched and/or multibranched alkanes and retaining in the adsorption zone at least said normal alkanes, wherein said adsorption zone contains a zeolite selected from the group consisting of 5A, MCM-22, silicalite, ZSM-5, ion exchanged HZSM-5 and mixtures thereof,
(c) withdrawing from said distillation stage a stream containing said diluent liquid solution and returning said stream to step (a).

Thus, the distillation in the presence of an adsorbent, particularly a solid zeolite adsorbent, enables in a simple manner the separation of mono-branched and/or multibranched isomers from the isomerate mixture, since both distillation and adsorption are conducted in the same column. Accordingly, the process may be regarded as an "adsorptive isomer distillation" operating in batch mode or semi-continuous mode such as swing operation.

The isomerate mixture may further comprise cyclic alkanes such as naphthenes, olefins and aromatic compounds such as benzene and toluene. The distillate stream will then also contain these compounds.

When said isomerate mixture (feed) contains cyclic alkanes such as naphthenes, these will be withdrawn in the distillate stream. This contrasts conventional distillation schemes, where such high boiling compounds are withdrawn from the distillation column bottom.

In step (b), by retaining in the adsorption stage at least said normal alkanes is meant that apart from normal alkanes, other compounds may be retained in the adsorbent, particularly mono-branched alkanes.

In a preferred embodiment of the invention step (a) comprises the steps of combining a first stream containing said isomerate mixture with a second stream of said diluent liquid solution having a boiling point which is higher than that of the isomerate mixture and passing the combined stream to said distillation stage. Thus, a diluent stream is withdrawn from the reactor and combined with the isomerate feed prior to entering the distillation unit containing the adsorbent.

It would be understood that the isomerate mixture and the diluent liquid solution may also be fed separately to the distillation column. Hence, the combination of a first stream containing the isomerate mixture with a second stream of a diluent liquid solution having a boiling point which is higher than that of the isomerate mixture may be conducted in a feeding region within the distillation column prior to the combined stream being exposed to the actual distillation stage or even in the immediate vicinity of the column, for instance in a mixing chamber in fluid communication with the distillation column.

In another embodiment, in step (a) the diluent liquid solution is contacted with the first stream containing the isomerate mixture in counter-current mode in a distillation column comprising an adsorbent in an adsorption zone by withdrawing a stream of diluent from the bottom of the distillation column and returning said stream to the top of the column. In this manner the isomerate and diluent are combined within the distillation column as they pass counter-currently therein, thereby providing a much simpler construction of the column. There is no need for combining the streams before entering the column. Further, the introduction of the diluent at the top of the column secures full wetting of the column. The isomerate feedstock may advantageously be fed in undiluted form to a position between 5% to 50%, preferably about 10% to 30% from the column bottom. This enables a very good use of the zeolite adsorption capacity which, unexpectedly, approaches static room temperature adsorption conditions. In other words, despite the dynamic nature of the process, the adsorption capacity of the adsorbent approaches what is achieved under equilibrium conditions in a steady-state situation.

It would also be understood that instead of a single distillate stream, a number of distillate streams may be withdrawn from the column, and several adsorptive distillation columns with different adsorbents may be combined in series to improve the separation.

Although it is difficult to make a straightforward comparison with i.e. a chromatographic process such as that of U.S. Pat. No. 6,353,144, where a different feedstock is used and several streams are eluted from the adsorber, the present invention involves, as indicated above, a much better use of the adsorption capacity of the zeolite: the chromatographic method has an apparent capacity of 0.015 g feed/g adsorbent based on the described flow rate, time in service and the adsorbent mass in the individual columns, whereas the adsorptive distillation according to the pre-sent invention may treat about 0.2 g feed/g adsorbent before regeneration and still achieve a higher separation factor as defined below. In addition, the present invention enables the utilisation of the same column for 2-3 hrs, while the chromatographic method of U.S. Pat. No. 6,353,144 describes a charge time of 50 seconds/column between regenerations.

By the invention, the selectivity on the removal of normal alkanes increases dramatically. The selectivity is measured in terms of a separation factor (SF), which as used herein is defined by a weight ratio according to the following expression:

$$SF = \frac{([\text{Mono-and/or multi-branched alkanes}]/[\text{normal alkanes}])_{product}}{([\text{Mono-and/or multi-branched alkanes}]/[\text{normal alkanes}])_{feed}}$$

For isomerate mixtures comprising methylcyclohexane (MCH) and n-heptane (n-$C_7$), average separation factors in the range 60-300 have been achieved over a 3 hrs period with maximum values as high as 2000. This represents a dramatic improvement with respect to prior art techniques, such as that described in U.S. Pat. No. 6,353,144, where the average separation factor between dibranched and n-alkanes (of a large isomer span) is at most 16 in periods of active adsorption of 50 sec depending on the chromatographic regeneration-elution procedure.

Without being bound by any theory it is believed that the presence of the diluent having a boiling point which is higher than the isomerate mixture contributes to a highly efficient distribution of heat and mass within the distillation column, while the vapour pressure of the diluent still dominates. The temperature in the column being well above the boiling points of the $C_7$ isomerate components (approx. 80-105° C.) allows for establishing a vapour-liquid equilibrium in the column, where the adsorbates (primarily n-$C_7$) are believed to be adsorbed from the liquid phase.

Inside the zeolite channels, diffusion may proceed in the gas phase and by capillary condensation. The preferential adsorption of specific components will shift the phase equilibrium such that there will be equilibrium for non-retained components, while the adsorbed species will be continuously extracted into the liquid phase. Relative to the gas phase the adsorption from the condensed phase will emulate a higher concentration of molecules/volume, which is equivalent to a hypothetical pressure increase. This gives rise to an increase in adsorption.

In this manner the process works in a way as a very well controlled gas-phase adsorption, in which the gas phase is generated in the distillation column and the residence time is extended because of the liquid phase that also prevails within the column. The vapour-liquid equilibrium will further affect the adsorption-desorption equilibrium, which may have a benefit compared to an overall-gas phase process. At the same time the void volume is occupied due to the presence of the liquid diluent solution contributing to the performance of the column. Hence, by the invention we are able to minimize the void volume (adsorbent-free volume) of the column.

The hydrocarbon stream containing the isomerate mixture to be treated stems normally from an isomerisation process, where it is required that non-isomerised compounds which are separated are recycled to the process. By the invention it is possible to produce isomerate streams of high octane number (high RON/MON) and to reduce the volume of the recycle stream containing non-isomerised compounds, such as n-heptane, to the isomerisation process. Accordingly, the economy of the isomerisation process is significantly improved. Furthermore, the invention enables the removal of methylcyclohexane (MCH), which particularly in the case of treatment of recycle streams for isomerisation units is highly undesirable, since this compound is a coke precursor in said process.

The adsorbent is preferably a solid adsorbent, such as a zeolite. Accordingly, the adsorption of the distillation stage is conducted in an adsorption zone containing a zeolite selected from the group consisting of 5A, MCM-22, silicalite, ZSM-5 preferably with a Si/Al-molar ratio of between 25 and 400, ion exchanged HZSM-5 and mixtures thereof. Such zeolites have the required geometry, i.e. pore mouth and channel dimensions allowing optimal interaction between adsorbent and adsorbate. The zeolite geometry at pore mouth ("portal") level normally determines the selectivity between isomers in adsorption based processes. Not only should one determine the fit between molecule and zeolite by critical diameters and cross section diameters, but other molecular parameters should be involved as well to make the appropriate selection. A promising approach is by applying the recent method by Gounaris et al., *Chemical Engineering Science* 61 (2006) 7933-7948, where both the calculated molecular footprint and the strain on the molecule in very close molecule-zeolite portal fits will determine the penetration of the molecule especially in asymmetric zeolites. Especially in situations where mono-branched species have to be separated from multibranched the asymmetric aspect is of relevance. In general, cross section dimensions in the range of 5.0 to 5.5 Å for the minor axis and 5.5 to 6.0 Å for the major axis as described in the art are normally suitable for separation of n-alkanes and branched isomers. Other suitable adsorbents with pore geometry having selectivity for n-alkanes and/or mono-branched isomers may thus include MFI types like ZSM-11, ZSM-12, ZSM-23, ZSM-35, ZSM-48 and other alumino-silicates as well as ferrierite, MAPO-31, SAPO-5 SAPO-11, SAPO-31 and EU-1.

According to a particular embodiment, in order to facilitate the separation and prevent undesired accumulation of heavy components from the isomerate mixture in the diluent, such heavy components (components with boiling temperatures above 110-120° C.) are removed by subjecting the hydrocarbon mixture to an initial conventional distillation step, known in the art as a "heart cut" distillation, i.e. prior to the adsorptive distillation. Because of the reduced accumulation of high boiling components in the diluent, there is no need for a diluent (solvent) regeneration step, which is otherwise required to maintain the narrow boiling range of the diluent.

Upon use, the adsorption capacity in the adsorption zone of the distillation column decreases and therefore, a regeneration mode is provided to re-establish the adsorption capacity of the adsorbent by treatment with a desorbent that will specifically remove the adsorbate (e.g. normal alkanes) for further recovery and upgrading. Accordingly, the process comprises further desorbing the adsorbed alkanes from the adsorption zone by passing a desorbent stream through said adsorption zone and withdrawing a stream containing at least normal alkanes. Other components in this stream may include mono-branched alkanes, which are also trapped by the adsorbent. The group of components retained in the column and subsequently desorbed can be expanded depending on the adsorbent.

The desorbent may be any suitable compound that is capable of regenerating the adsorbent by removing the adsorbed alkanes from the adsorbent, such as hydrogen, nitrogen, isopentane, n-pentane, methane, n-butane, isobutane or mixtures thereof. Preferably, the desorbent is a stream of n-pentane or n-butane or a mixture of both compounds. The desorption (regeneration) may be performed according to any desorption technique known in the art. It may comprise desorption in the liquid state, i.e. at pressures above the saturation point of the desorbent in the gas phase or in combination in which the pressure is regulated to operate in both liquid and gas phase. The operating pressure is preferably varied, while keeping the temperature of the distillation unit as constant as possible (isothermal). We have found that although the desorbent, for instance some n-pentane, may be present in the adsorbent upon reuse in a subsequent adsorption step, the performance of the adsorbent is unaffected during the adsorptive distillation, while significant amounts of n-pentane are distilled off.

In yet another embodiment of the process, prior to passing a desorbent stream through the adsorption zone, the diluent is removed from the column. This enables a better contact between desorbent and zeolite in the column during the desorption (regeneration) step.

According to the invention, the diluent liquid solution is preferably substantially free of isomers and is a solution of compounds selected from the group consisting of compounds comprising methyl, ethyl and propyl substituted benzenes and methyl, ethyl and propyl substituted naphthenes boiling in the range from 135° C. to 200° C., in particular xylene, cumene, mesitylene, pseudocumene, durene, decalin and mixtures thereof.

A preferred diluent is mesitylene, since it has been found to give the highest efficiency particularly when treating $C_7$ isomerates. When operating with mesitylene, which has a boiling point of 165° C., the preferred process temperature of the distillation step is in the range of 140-160° C., that is 5° C. to 25° C. below the boiling point of the diluent depending on the process scheme and column feed point of isomerate and diluent. The relative lowering of the temperature during the distillation stage has been found to improve the distillate quality in terms of lowering the content of mesitylene in said distillate and also in terms of energy efficiency due to savings on the heat load. However, lowering the temperature too much may negatively affect the process. For instance, when using mesitylene as the diluent, isothermal column temperatures below 135° C. have shown no distillate production. Accordingly, the adsorption is preferably conducted at around the boiling point of the diluent liquid or the distillation temperature of the diluent-isomerate mixture, preferably at temperatures not more than 20° C. below the boiling point of the diluent liquid or the distillation temperature of the diluent-isomerate mixture.

In a further embodiment of the process the isomerate mixture comprising normal alkanes, mono-branched alkanes, multi-branched alkanes and cyclic alkanes (such as naphthenes) is a $C_7$-isomerate cut comprising n-heptane and methylcyclohexane (MCH). By the invention it is possible to treat hydrocarbon streams containing different isomerate cuts, like any mixtures of $C_5$ to CB alkanes, such as $C_8$ to $C_7$, $C_6$ to $C_7$, $C_6$ to $C_8$, or $C_8$, but more particularly intermediate $C_7$ cuts. The separation of isomers from such intermediate cuts of $C_7$-alkanes is particularly challenging since this cut represents a particularly low octane group comprising mono-branched isomers, which are significantly difficult to separate from the straight chain isomers (normal alkanes) while recovering the multi-branched isomers. The process according to the invention enables high selectivity in the separation of e.g. MCH (boiling at 101° C.) as distillate with respect to n-$C_7$ (boiling at 98° C.), which is in turn retained in the adsorbent. As described above, the MCH content is particular advantageous to control in isomerisation processes as recycling of this compound increases the deactivation of isomerisation catalysts due to coking.

The diluent liquid solution is preferably withdrawn from the distillation column at the bottom and may be returned (recycled) to the feed of the distillation column where it may be combined with the isomerate mixture. We have achieved diluent streams at the bottom of the column representing 96% to 99.5% of the diluent feed (i.e. we recover up to 99.5% of the diluent), depending on the extent of dilution imposed on the feed isomerate mixture as well as the column temperature. The column temperature will determine the distillate leaving the column, but also the content of mesitylene in the distillate. The higher the temperature the more mesitylene is found in the distillate, and also the separation in terms of mass of distillate is increased. The mesitylene content in the distillate effluent can be diminished to values as low as 0.1 to 0.5 wt % by decreasing the temperature to no less than 145° C.

During the distillation, some of the highest boiling compounds of the isomerate mixture will be concentrated in the product being withdrawn at the top of the column. We have found that particularly high selectivities, i.e. high separation factors, are obtained when the weight percent of isomerate with respect to the diluent, preferably mesitylene, in the combined stream entering the distillation stage is 5% to 50%, preferably 10% to 30%, more preferably 15% to 25%, such as at about 20%.

As described previously, instead of a single adsorptive distillation column, several adsorptive distillation columns with different adsorbents may be combined in series to improve the separation. In a particular embodiment, the process of the invention is conducted in a series arrangement in which the distillate stream of a first distillation stage is used as feed in a second distillation stage. Preferably the isomerate mixture passed to the first distillation stage is a $C_7$-isomerate cut comprising n-heptane (n-$C_7$) and methylhexane, particularly methylhexane in the form of 2-methylhexane (2 MH) and 3-methylhexane (3 MH), in which the adsorption zone in the first distillation stage contains a zeolite 5A and the adsorption zone in the second distillation stage contains a ZSM-5 zeolite. Hence, in the first distillation stage the zeolite 5A retains said n-heptane, while the distillate stream with reduced content of n-heptane and containing methylhexanes is used as feed in a second distillation stage in which the adsorption zone contains a ZSM-5 zeolite, which is a zeolite that more specifically retains methylhexanes, in particular 2-methylhexane (2 MH) and 3-methylhexane (3 MH). Further, we have found that in order to separate methylhexanes from the isomerate, n-heptane separation has to be conducted prior to the methylhexane separation process, since n-heptane is stronger retained on narrow pore mouth zeolites than methylhexanes. Accordingly, we avoid the presence of any n-heptane left that may act as desorbent.

By combining two zeolites according to the invention it is therefore possible to generate separate streams of higher concentrations of specific isomers, e.g. a concentrated stream of methylhexanes, and a concentrated stream of n-heptane. The concentrated stream of methylhexanes and the concentrated stream of n-heptane can be passed to separate reactor units in an isomerisation process, where it is possible to expediently conduct the isomerisation of n-heptane, particularly because such isomerisation occurs via methylhexane.

In yet another embodiment of the invention aromatic compounds, in particular benzene, are separated from other compounds in a hydrocarbon mixture containing said aromatic compounds. We have found that the zeolite adsorbent may also be selected so that it can retain aromatic compounds like benzene while distilling other hydrocarbons. Accordingly, we provide a process for the separation of benzene from other hydrocarbons in a hydrocarbon mixture, the process comprising:

(a) passing said hydrocarbon mixture to a distillation stage, said distillation stage comprising an adsorbent in an adsorption zone which is in contact with a diluent liquid solution having a boiling point which is higher than that of the hydrocarbon mixture,
(b) withdrawing from said distillation stage a distillate stream containing other hydrocarbons than benzene and retaining benzene in the adsorption zone, wherein said adsorption zone contains zeolite X, zeolite Y, or mixtures of both,
(c) withdrawing from said distillation stage a stream containing said diluent liquid solution and returning said stream to step (a).

Said other hydrocarbons include mainly toluene, n-alkanes, branched alkanes, olefins and other unsaturated hydrocarbons, as well as cyclic hydrocarbons. The hydrocarbon mixture may be a gasoline stream, whereby benzene removal has to be achieved down to levels as low as one percent or less.

The adsorption of the distillation stage is preferably conducted in an adsorption zone containing a ion exchanged zeolites X and Y, or mixtures thereof, particularly zeolites selected from the group consisting of NaX, NaY and mixtures thereof, in which the NaX and NaY zeolites have a Si/Al-molar ratio of below 20, most preferably Si/Al-molar ratio below 3.

A particularly important compound that falls within the term "other hydrocarbons" is toluene. Due to environmental regulations it has recently become more and more necessary to separate benzene in hydrocarbon mixtures without the simultaneous separation of toluene, particularly when treating naphta cuts. Thus, in a particular embodiment the hydrocarbon mixture is preferably a mixture comprising at least 0.1 wt % benzene and toluene, more preferably a naphta cut containing benzene and toluene, in which benzene and toluene combined represent at least 0.1 wt % of the hydrocarbon mixture. The naphta cut may be a FCC or a coker naphta cut as both contain significant amounts of benzene and toluene. Yet, in order to facilitate the separation and prevent undesired accumulation of heavy components from the hydrocarbon mixture in the diluent, the hydrocarbon mixture may be depleted of such heavy components (components with boiling temperatures above 115° C.) by subjecting the hydrocarbon mixture, such as a naphta cut to an initial conventional distillation step, that is a "heart cut" distillation as in the case of separation in isomerate mixtures. Because of the reduced accumulation of high boiling components from the hydrocarbon mixture in the diluent, there is no need for a diluent (solvent) regeneration step, which is otherwise required to maintain the narrow boiling range of the solvent.

In a particular embodiment, the relative amount by weight of toluene to benzene in the hydrocarbon feed is in the range 1 to 10, preferably 2-7, more preferably 5; that is, the amount of toluene in the feed may be 1-10 times higher, preferably 2-7 times higher that that of benzene, for instance 5 times higher.

Preferably, step (a) comprises the steps of combining a first stream containing said hydrocarbon mixture with a second stream of said diluent liquid solution having a boiling point, which is higher than that of the hydrocarbon mixture and passing the combined stream to said distillation stage. Thus, the diluent stream is withdrawn from the reactor and combined with the hydrocarbon feed (hydrocarbon mixture containing benzene) prior to entering the distillation unit containing the adsorbent.

In another embodiment, in step (a) the diluent liquid solution is contacted with the first stream containing the hydrocarbon mixture in counter-current mode in a distillation column comprising an adsorbent in an adsorption zone by withdrawing a stream of diluent from the bottom of the distillation column and returning said stream to the top of the column. This enables, as in the embodiment with the isomerate mixture, a much simpler construction of the column since there is no need for combining the streams before entering the column, and additionally the introduction of the diluent at the top of the column secures full wetting of the column.

The diluent liquid solution is preferably a solution of compounds selected from the group consisting of benzene substituted with 1, or 3 to 6 methyl, ethyl or propyl groups, such as cumene, pseudocumene, mesitylene, and mixtures thereof. Similarly to the situation in which the feed consists of an isomerate mixture, the separation of benzene and toluene is better achieved when utilizing mesitylene (1,3,5 trimethylbenzene) as the diluent. In particular, the higher the content of mesitylene in a benzene-toluene feed the higher the separation factor. The separation factor is in this case calculated as follows:

$$SF = \frac{([\text{Toluene}]/[\text{Benzene}])_{product}}{([\text{Toluene}]/[\text{Benzene}])_{feed}}$$

By contrast, increasing the content of another diluent such as decalin has no effect on the separation factor. Preferably the weight percent of the benzene-toluene feed with respect to mesitylene is below 30%, more preferably below 20%, with the highest separation factors obtained at 10%.

In order to regenerate the adsorbent by removing the adsorbate (benzene) a desorption step may also be conducted. Accordingly, the process further comprises desorbing the adsorbed benzene from the adsorption zone by passing a desorbent stream through said adsorption zone and withdrawing a stream containing benzene. The desorbent is preferably a hydrocarbon containing at least 50 wt % cyclohexane. Cyclohexane offers the advantage that it may be generated expediently by hydrogenation of the retained benzene ex-situ, i.e. in a separate stage, for instance in close proximity to the process plant in which benzene is being separated.

In a preferred embodiment, prior to passing the desorbent stream through the adsorption zone, the diluent is removed from the column. This enables a better contact between desorbent and zeolite in the column during the desorption (regeneration) step.

In yet a further embodiment of the invention paraffins in particular propane are separated from olefins, particularly propylene in a hydrocarbon mixture containing said paraffins and olefins. We have found that the zeolite adsorbent may also be selected so that it can retain paraffins like propane while distilling propylene and other olefins. Normally propylene is separated from propane by conventional distillation processes, which however are highly expensive because of the high demand on propylene purity in down-stream processes such as polymerisation to polypropylene, where propylene purity needs to be as high as 99.7 wt %. Although it is possible to expediently achieve a certain degree of propylene purity, e.g. op to 80-90% by conventional distillation, the costs involved in the last purification stage op to 99.7% by conventional distillation are simply too high due to the high energy requirements in the process. It would be desirable to be able to provide an alternative and more expedient process to separate olefins from paraffins, particularly to generate pure olefinic streams for downstream processes, and more particularly to generate propylene rich stream from propane-propylene fractions.

Accordingly, we provide a process for the separation of paraffins from olefins in a hydrocarbon mixture, the process comprising:
(a) passing said hydrocarbon mixture to a distillation stage, said distillation stage comprising an adsorbent in an adsorption zone which is in contact with a diluent liquid solution having a boiling point which is higher than that of the hydrocarbon mixture,
(b) withdrawing from said distillation stage a distillate stream containing olefins and retaining paraffins in the adsorption zone, wherein said adsorption zone contains zeolite X, zeolite A or mixtures of both,
(c) withdrawing from said distillation stage a stream containing said diluent liquid solution and returning said stream to step (a).

Preferably the process involves the separation of the paraffinic compound propane from olefins in said hydrocarbon mixture. Thus, the paraffin retained in the adsorption zone will be mostly propane, while the olefins will leave in the distillate stream. The separation of propane from propylene in a propane-propylene fraction is of particular relevance. Such fraction may be obtained by a prior conventional distillation up to a given propylene purity, for instance op to 80-90% prior to conducting a final adsorptive distillation stage or stages according to the present invention. Such prior distillation stage or initial distillation stage serves also to remove heavy components in the hydrocarbon mixture feed that may accumulate in the diluent.

When treating paraffin-olefin hydrocarbon mixtures, the adsorption of the distillation stage is preferably conducted in an adsorption zone containing zeolites 13×, zeolites 3A, 4A, 5A or mixtures thereof. The zeolites may also be ion exchanged.

Preferably, step (a) comprises the steps of combining a first stream containing said hydrocarbon mixture with a second stream of said diluent liquid solution having a boiling point, which is higher than that of the hydrocarbon mixture and passing the combined stream to said distillation stage. Thus, the diluent stream is withdrawn from the reactor and combined with the hydrocarbon feed (hydrocarbon mixture containing paraffins and olefins) prior to entering the distillation unit containing the adsorbent.

In another embodiment, in step (a) the diluent liquid solution is contacted with the first stream containing the hydrocarbon mixture in counter-current mode in a distillation column comprising an adsorbent in an adsorption zone by withdrawing a stream of diluent from the bottom of the distillation column and returning said stream to the top of the column. This enables, as in the embodiment with the isomerate mixture or benzene other hydrocarbon mixture, a much simpler construction of the column since there is no need for combining the streams before entering the column, and additionally the introduction of the diluent at the top of the column secures full wetting of the column.

When treating paraffin-olefins hydrocarbon mixtures the diluent liquid solution is also preferably a solution of compounds selected from the group consisting of benzene substituted with 1, or 3 to 6 methyl, ethyl or propyl groups, such as cumene, pseudocumene, mesitylene, and mixtures thereof. As in the previous embodiments involving other hydrocarbon mixtures (feeds), the most preferred diluent liquid solution is a solution of mesitylene (1,3,5 trimethylbenzene).

Regardless of whether the feed consists of an isomerate mixture comprising alkanes and branched alkanes, or a hydrocarbon mixture comprising aromatic compounds where benzene has to be separated from other hydrocarbons, in particular toluene, or a paraffin-olefin hydrocarbon mixture such as propane-polyethylene fraction, it would be desirable to enhance the dynamics of the adsorption. Accordingly, in order to decrease the adsorption time of the column, i.e. time to exhaustion of capacity, the level of the high boiling diluent in the column, particularly mesitylene, is controlled. Instead of a substantially filled column there are advantages in using a less filled column, since this avoids flooding and excessive diluent hold up in when operating the column in the counter-current recycle mode. The performance of the column is then a balance between the diluent level in the column, the diluent recycle rate and the feed rate. When the diluent level is lowered the recycle rate has to be increased to ensure wetting of the adsorbent. Higher flow rates of feed and higher recycle flow rates will lead to liquid hold up and increase the level of diluent in the distillate. Excessive feed rates lead to flooding of the column with the diluent being unable to trickle down the column. We have found that where the process is operated in counter-current mode thereby initially wetting the adsorbent from above the column and the diluent level is kept equal to or below the isomerate or hydrocarbon mixture feed point and 5-20% from the column bottom, preferably about 10% from the column bottom, the recycle rate could be increased by a factor 4-7 and the feed rate could then be increased by a factor 3 without increasing the diluent content in the distillate. As a result the adsorption time of the column could be decreased by at least a factor 3, thereby significantly improving the dynamics of the adsorption. The isomerate or hydrocarbon mixture feed point is at position 5% to 50%, preferably about 10% to 30% from the column bottom.

As used herein the term column bottom represents the lowest point of the apparatus used in the adsorptive distillation of the present invention.

The invention encompasses also the apparatus for carrying out the process. Accordingly, we provide a distillation column being heated along the entire or part of its length, comprising inlet means for the passage of separate streams of feed mixture and diluent liquid solution or inlet means for the passage of a combined stream of feed mixture and diluent liquid solution, outlet means for withdrawal of at least one distillate stream, outlet means for the withdrawal of a stream of a liquid solution containing said diluent, inlet means for the passage of a desorbent stream and outlet means for the withdrawal of a depressurized desorbent stream, wherein an adsorption zone packed with solid adsorbent material is arranged within said column.

The term "feed" encompasses an isomerate mixture comprising normal alkanes mono-branched alkanes, multi-branched alkanes and cyclic alkanes or a hydrocarbon mixture containing benzene to be separated, or a paraffin-olefin hydrocarbon mixture, particularly a propaene-propylene fraction. The feed may have been subjected to an initial conventional distillation step in order to remove heavy components that may accumulate in the diluent as described above.

The distillation column may further comprise a feeding region, where the mixing of feed and diluent is conducted. This is particularly suitable when said feed mixture and diluent are fed separately to the distillation column.

DETAILED DESCRIPTION

Figure 1:
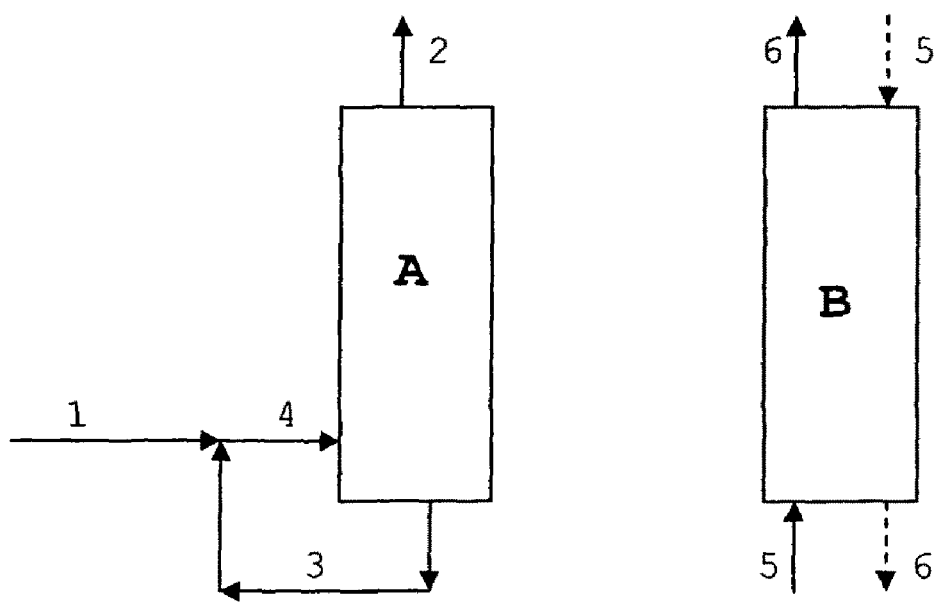
FIG. 1 shows a schematic of the distillation column in adsorption and desorption mode according to one embodiment of the invention in which the isomerate feed mixture and diluent are combined prior to entering the column.

FIG. 1 shows a schematic of the adsorption mode A and desorption mode B according to one embodiment of the process. During adsorption and simultaneous distillation, an isomerate mixture 1 is combined with a diluent solution 3 to form a combined feed-diluent stream 4. The combined stream 4 enters the distillation column having disposed an adsorption zone therein. A distillate containing MCH, multi and/or monobranched alkanes is withdrawn from the top as stream 2. By controlling the temperature of the column, the diluent can almost entirely be directed to the bottom and be withdrawn as effluent stream 3. In the adsorption zone of the column, n-alkanes are retained. The group of components retained can be expanded depending on the adsorbent. The effluent 3 of diluent liquid withdrawn at the bottom of the column is recycled and combined with the feed isomerate mixture 1. During the desorption step B, a stream 5 of a suitable desorbent such as pentane is injected. Pressure can be selected to perform this in the liquid or the gaseous state. The desorbent stream carrying the desorbed material (n-alkanes and/or mono-branched alkanes) will leave the top of the column as stream 6 in the co-current desorption mode. In counter-current desorption the desorbent is injected from the top 5' and leave with the desorbed components at the bottom of the column 6'.

Figure 2:
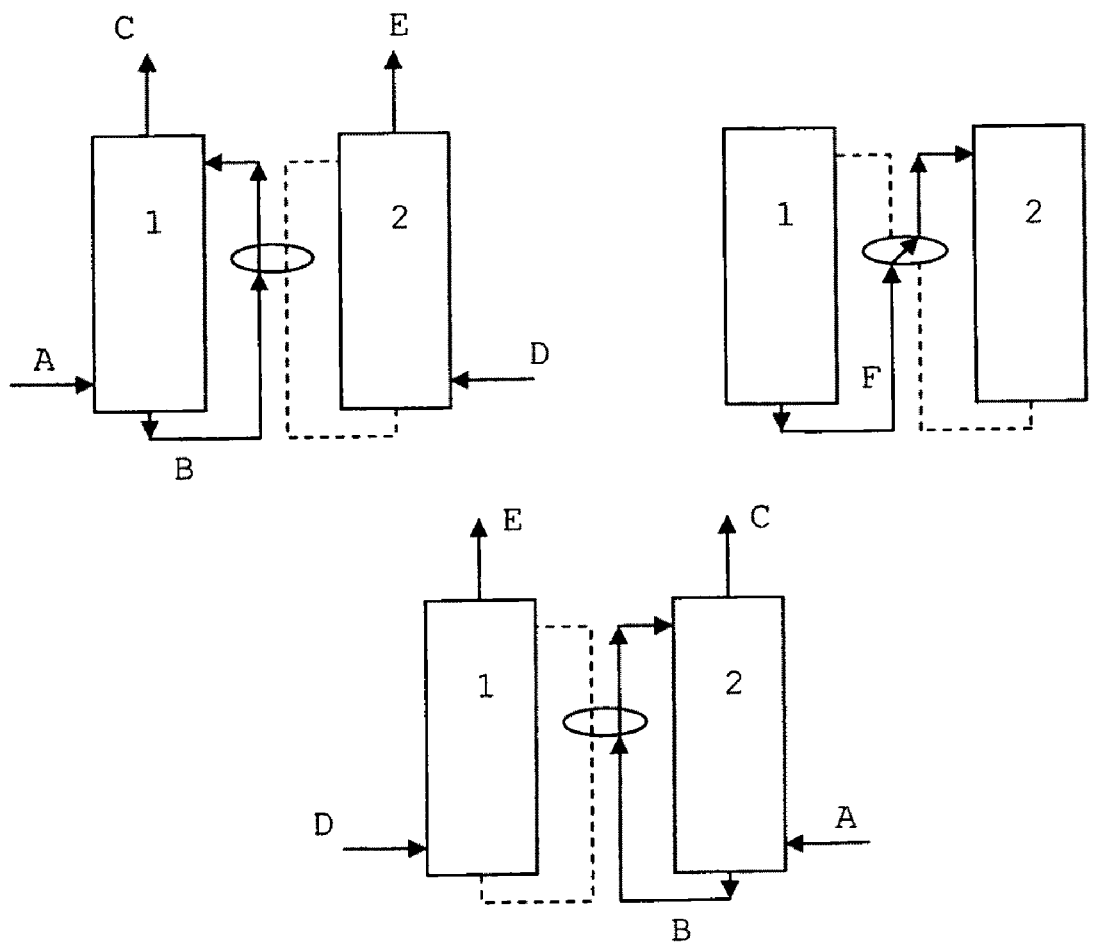
FIG. 2 shows a schematic of the distillation column in adsorption and desorption mode according to another embodiment of the invention in which the diluent is recycled directly to the top of the column.

In FIG. 2 the process runs with a direct recycle of the diluent from bottom to top. The figure shows a schematic description of the combination of two columns, where one column 1 operates in the absorption mode and the other column 2 in the desorption mode. A is the feed point for isomerate, while B serves as the high boiling diluent solvent recycle that returns to the top of the column. The distillate stream C containing very low concentrations of the adsorbate (straight chain and/or mono-branched isomers) and low concentration of the high boiling diluent solvent added is withdrawn at the top. During the adsorptive distillation in column 1, column 2 is regenerated and the adsorbate is desorbed by pumping a stream D of desorbent and by withdrawing a stream E of desorbent and adsorbate from the top of the column. The desorbent may be in the liquid or in the gaseous state. At the end of the adsorptive distillation step in column 1, the diluent stream F is pumped from the bottom of column 1 to the top of regenerated column 2 filling this column with the diluent and emptying column 1. This enables a better contact between desorbent and zeolite in column 1 during the desorption and regeneration step. The adsorptive distillation proceeds subsequently in column 2, while the desorption step is conducted in column 1.

Figure 3:
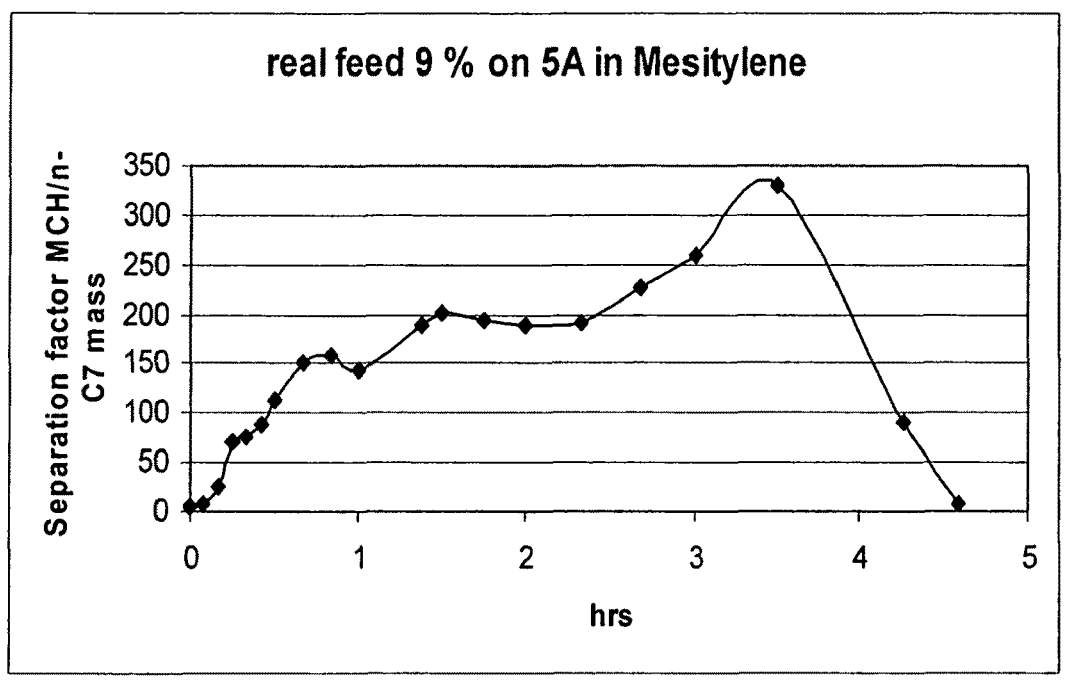
FIG. 3 shows a graph of the selectivity in terms of separation factor of MCH from an isomerate feed diluted with mesitylene.

FIG. 3 shows a graph of the selectivity in terms of separation factor of MCH from an isomerate mixture diluted 9 wt % with mesitylene over a zeolite 5A adsorbent. The C7 isomerate mixture represents a real feed having a number of mono and multi-branched as well as about 20 wt % n-heptane. It is seen that after a few hours of operation in the distillation column the selectivity for MCH in the distillate top product gradually increases reaching its maximum after about 3-4 hours with a separation factor above 300. A decline in separation factor at the end of the operation is observed as the adsorbent capacity is exhausted. The column was operated at a temperature close to the boiling point of mesitylene resulting in that the distillate had a significant content of mesitylene. As mentioned above, this can be avoided by operating the column at lower temperatures.

Figure 4:
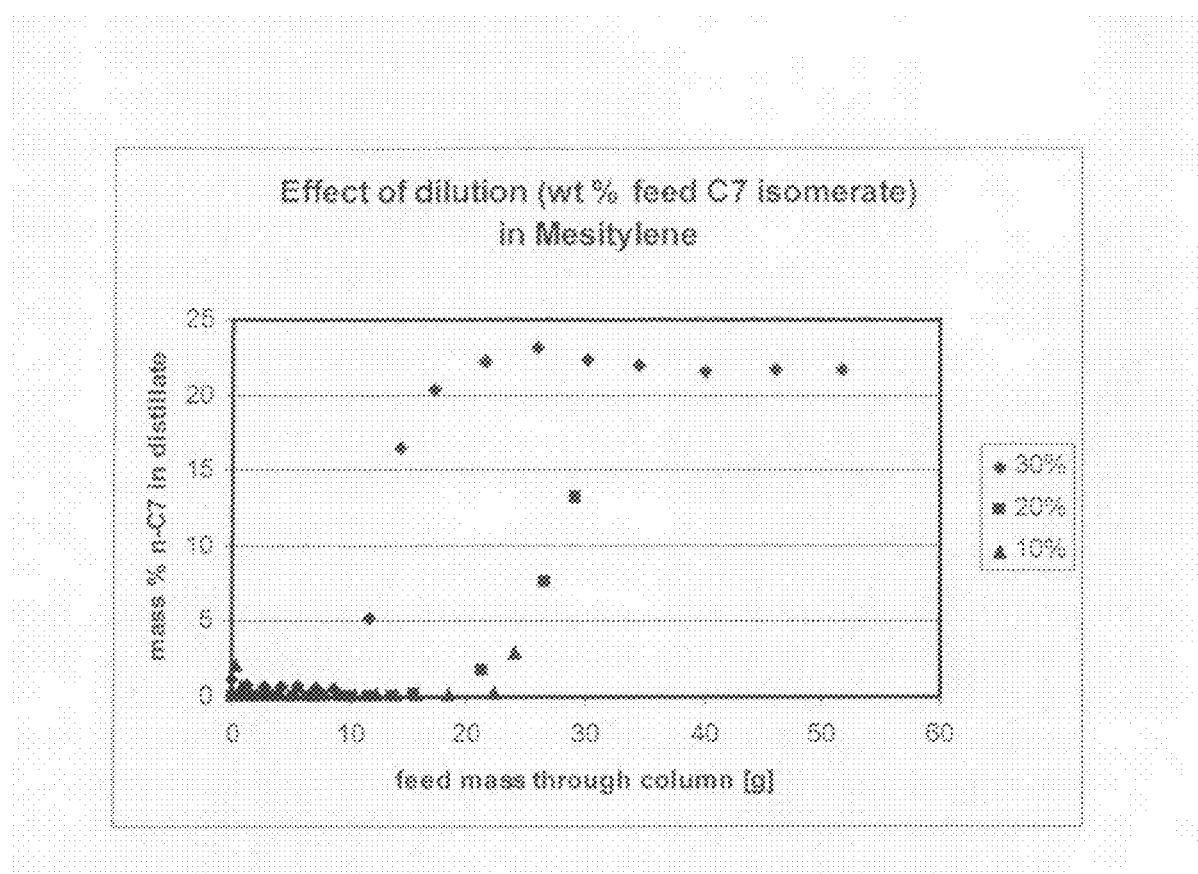
FIG. 4 is a graph showing the effect of dilution of the isomerate feed in mesitylene.

FIG. 4 shows the effect of dilution of the isomerate feed in mesitylene on distillate composition over a zeolite 5A adsorbent. The weight percent of isomerate in mesitylene is indicated in the graph. When the weight percent of isomerate in the liquid mesitylene solution in the combined stream entering the distillation stage is 10% the maximum value of the separation factor SF is about 250 increasing drastically to a maximum value of about 2000 when said weight percent is about 20% but decreasing sharply to a maximum value of about 40, when the weight percent of the isomerate in the diluent mixture increases to 30%.

Figure 5:
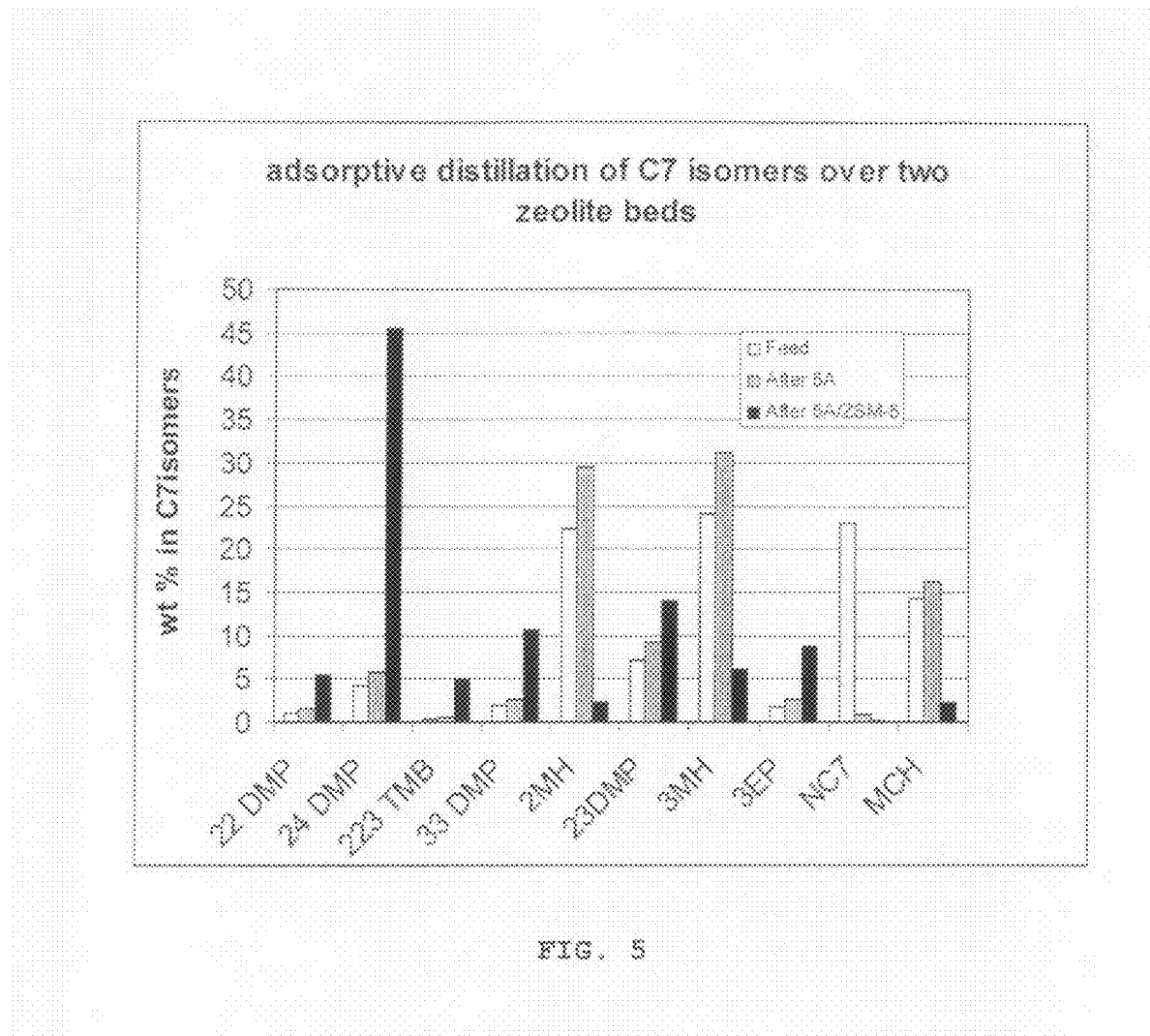
FIG. 5 is a graph showing the composition of isomers, particularly methylhexanes (MCH) in the distillate stream after adsorptive distillation in one or two stages.

FIG. 5 shows the effect of operating with a single distillation stage compared with a series arrangement and combining zeolites. For the particular and relevant case of methylhexanes (2 MH and 3 MH) with respect to n-heptane (n-$C_7$ NC7), it is found that these methylhexanes are not retained by the zeolite of the first stage (5A), whereas n-heptane is almost completely retained. The distillate stream with reduced n-heptane after being passed through a second distillation stage with zeolite ZSM-5 as the adsorbent results in the retention of the methylhexanes, thus enabling the generation of separate concentrated streams of n-heptane and methylhexanes. Thus, the desorbate obtained from the two columns consisting mainly of n-heptane and methyhexanes may be recycled to a hydroisomerisation unit to convert these into multibranched isomers. In terms of octane number, the effect of conducting this sequential separation with removal of the three low RON compounds n-heptane, 2-methylhexane and 3-methylhexane is an increase of RON in the final distillate stream of 31 units.

Figure 6:
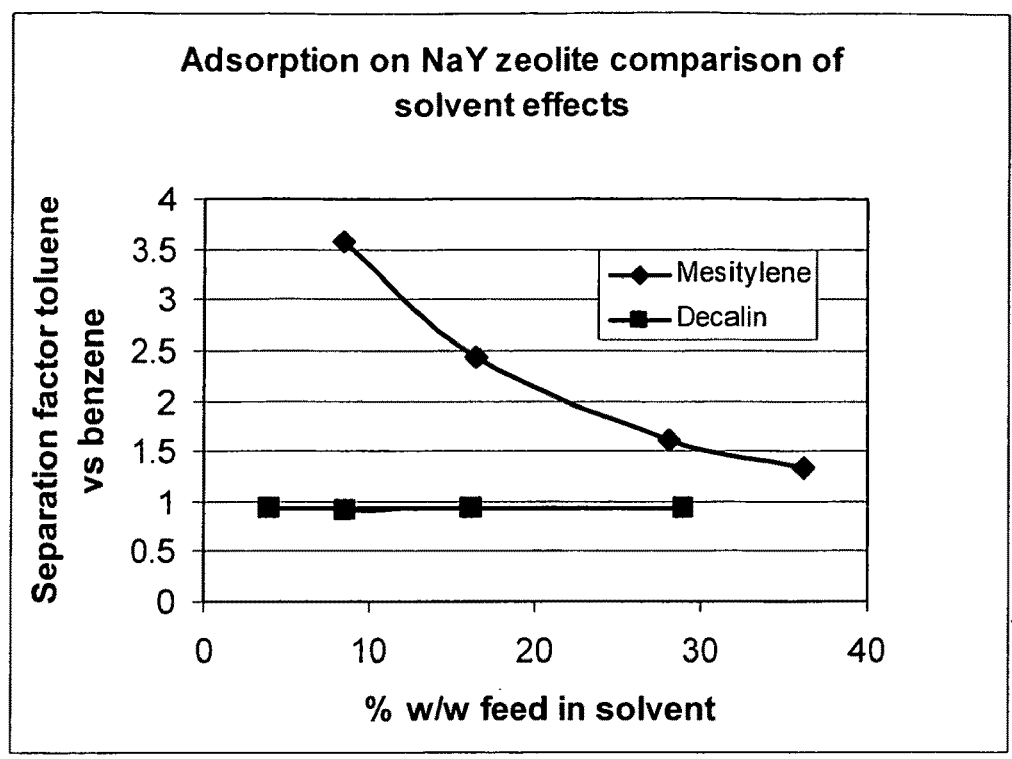
FIG. 6 is a graph showing the separation of benzene and toluene over NaY zeolite by using the diluents mesitylene and decalin.

FIG. 6 shows the effect of dilution of a benzene-toluene feed with the diluents (solvents) mesitylene and decalin. The weight percent of the benzene-toluene mixture in mesitylene or decalin is indicated in the graph. While decalin shows no effect on the separation factor, the higher the content of mesitylene or conversely the lower the content of benzene-toluene with respect to mesitylene, the higher the content of toluene in the distillate with respect to benzene with benzene being preferably retained in the zeolite.

EXAMPLES

Experiments were performed in a 90 cm fixed-bed zeolite column, which is used as a batch distillation unit heated along the entire length of the column. Two feeds were used: a real isomerate and a two-component mixture of n-heptane and methylcyclohexane (MCH). During the distillation, MCH being the highest boiling component of the two-component mixture is concentrated in the top product (boiling point MCH: 101° C., n-heptane: 98° C.). Mesitylene having a boiling point of 165° C. is used as diluent for the feed isomerate mixture. The dilution is in the range 10 wt % to 30 wt % feed in mesitylene. During the distillation, the diluent solvent is withdrawn from the bottom of the distillation unit and recycled. Zeolites extrudates of ZSM-5 and 5A were used as adsorbent materials in the distillation unit. Both adsorbents present a high selectivity for the n-alkanes as revealed by average separation factors of up to 225 over several hours of continued distillation.

Example 1

Selective production of distillate stream of low heptane concentration from model isomerate system using pre-mixed feed. A column loaded with 432 g of 5A zeolite extrudate was heated to 165° C. The column had previously been used and regenerated by n-pentane flooding. The feed comprising a combined stream having n-heptane (0.83 wt %), methylcyclohexane (3.4 wt %) and mesitylene (95.8 wt %) was injected at a position 25% above the column bottom. As the process proceeded over 4.5 hrs, 824 g of feed was introduced resulting in three streams with the following average composition as shown in Table 1, the balance of the distillate being made up by n-pentane from the desorption.

TABLE 1

| wt % | Distillate | Bottom draw | Void |
|---|---|---|---|
| n-$C_7$ | 0.135 | 0.015 | 0.008 |
| methylcyclohexane (MCH) | 30.409 | 1.325 | 1.402 |
| Mesitylene | 54.610 | 98.438 | 98.566 |
| Separation factors for MCH/n-$C_7$ | 55 | 22 | 42 |

As observed the mesitylene bottom draw has a low content of n-heptane and can be recycled as diluent for the feed. The distillate contains a large fraction of MCH which during the run is much higher than the final combined distillate reported in Table 1. The inter-pellet void volume of the column is at the end of the run flushed and results again in a high diluent purity. The adsorbed species were desorbed with liquid n-pentane. The highest separation factor for MCH and n-$C_7$ measured during the process was 230, while the average over 4.5 hrs as shown in the table (MCH/n-$C_7$) was 55. The initial first 30 minutes had an increasing trend in SF and a substantial n-pentane desorbent production. Although n-pentane was found in the distillate throughout the course of the test, this did not seem to severely affect the performance. However, we do know that much higher SF values are observed when operating a freshly loaded column, which has not been exposed to pentane. Due to the high column temperature in this test a substantial amount of mesitylene is bound to be found in the distillate. It is desirable and possible to control the column temperature at the top outlet to avoid mesitylene in the distillate. The present example runs with little mesitylene the first 1 hr, while the pentane content is high. Repeated experiments with different control of the top temperature shows that mesitylene content in the distillate effluent can be diminished to about 0.5 wt % by decreasing the temperature to no less than 145° C.

Example 2

Selective production of low heptane content distillate from real isomerate using pre-mixed feed. A mixture of 9% $C_7$ isomerate in mesitylene was charged to a column with pentane desorbed and regenerated 5A zeolite at a feed point 25% above the column bottom. The column temperature was isothermal and operated at 160° C. The compositions of feed and overall combined effluent streams are as given in Table 2.

TABLE 2

| Wt % | Feed | Distillate | Bottom draw | Void |
|---|---|---|---|---|
| n-$C_7$ | 1.76 | 0.05 | 0.05 | 0.30 |
| methylcyclohexane (MCH) | 1.10 | 2.02 | 0.31 | 0.43 |
| <n-$C_7$ | 5.37 | 10.47 | 0.63 | 1.30 |
| >n-$C_7$ (not incl. MCH) | 0.73 | 0.46 | 0.06 | 0.19 |
| n-pentane | 0 | 3.62 | 0.14 | 0.04 |
| mesitylene | 91.05 | 83.39 | 98.81 | 97.74 |

This experiment ran over a 4.5 hr period and hence represents a full loading of the zeolite with a capacity of 0.053 g n-heptane/g zeolite. Comparing this to a static room temperature capacity measurement of the zeolite of 0.050 g n-heptane/g zeolite the experiment shows that this process makes full use of the zeolite capacity despite of the use of much higher temperatures during the distillation. It is otherwise well known in the art that an increase in temperature greatly reduce the adsorption capacity of zeolites. The development of the separation factor between MCH and n-heptane is shown in FIG. 3.

Example 3

A column of freshly loaded zeolite 5A was fed 10% above the column bottom with a 6.5% C7 isomerate in mesitylene solution at 165° C. The average n-heptane content of the distillate after 3.5 hrs in service was 0.01 wt %. As only 11 g of heptane had passed the column due to the high dilution of the feed the capacity had not been exhausted and only approximately 40% of the capacity had been used. Due to the high temperature a substantial amount of mesitylene was also found in the distillate of this experiment.

Example 4

The above column was loaded with 426 g of zeolite 5A and the column was filled with mesitylene heated to 150° C. and the recycling from bottom to top was initiated at a low rate. At isothermal conditions the 100% feed isomerate was injected at a rate of approximately 50 g/hr for 3 hrs. The injection point was at 10% above the column bottom. The overall separation factor between MCH and n-$C_7$ was approx. 2100 over 3 hrs in service. Initial distillate (approx. 30 minutes) was more than 82% mono+multibranched. The first 10 minutes gave a multi-branched dominated distillate due to the temperature difference in boiling point between multi and mono-branched species. The feed and distillate composition is given in the Table 3 below. In this case the distillate made up 53% of the feed, as the desorption/regeneration step was initiated immediately after the adsorption mode with only a short post-distillation, hence a certain amount of the feed was never distilled from the column. The mass balance shows that 96% of the n-heptane was retained on the 5A zeolite. The active capacity for n-$C_7$ was 0.07 g/g zeolite. The n-heptane in the distillate results from the last 30 minutes of the distillation.

TABLE 3

| | <n-$C_7$ | n$C_7$ | MCH | Mesitylene | >n-$C_7$ |
|---|---|---|---|---|---|
| Feed | 59.4 | 19.5 | 12.1 | 0 | 9.0 |
| Distillate | 81.9 | <0.02 | 15.1 | 0.1 | 2.5 |

Example 5

To decrease the adsorption time (time to exhaustion of capacity) of the 90 cm×Ø3 cm column or any column operating in the same manner, the level of the high boiling solvent, in the present case mesitylene is controlled. While Example 4 describes the performance of a column initially filled (about 50%) with mesitylene, one may benefit from a less filled column to avoid flooding and excessive mesitylene hold up when operating in the counter-current recycle mode. The performance of the column is then a balance between the mesitylene level, the mesitylene recycle rate and the feed rate. When the mesitylene level is lowered the recycle rate has to be increased to assure wetting of the adsorbent. At a feed rate of 50 g/hr and an initial mesitylene level of 50% of the apparent void the recycle rate should be between 50 g/hr and 80 g/hr. Higher flow rates of feed and higher recycle flow rates will lead to liquid hold up and increase of mesitylene in the distillate. At excessive feed rates this leads to flooding of the column with mesitylene being unable to trickle down the column. A series of experiments were performed where the adsorbent was initially wetted from above and the mesitylene was drained off to a level equal to or preferably just below the isomerate feed point approximately 10% from the column bottom. The recycle rate could under these circumstances be increased to about 350 g/hr and the feed rate could then be increased up to about 170 g/hr without increasing the mesitylene content in the distillate. Hence the adsorption time of the column could be decreased by more than a factor 3.

Example 6

Yet another embodiment of the invention is the removal of benzene from toluene in a hydrocarbon mixture. Zeolites such as NaX and NaY preferably with a Si/Al ratio below 20 and better below 3 are particularly suitable for this separation process. In this separation the presence of toluene will affect the adsorption of benzene negatively in most cases and selectivity between the two compounds is small. Yet, upon dilution with mesitylene we have observed that the overall capacity for benzene is lowered but the selectivity (or separation factor) between benzene and toluene is increased up to 3. FIG. 6 shows the effect of dilution with mesitylene on the adsorption selectivity on NaY zeolite between the two compounds in a model system with 1% benzene and 5% toluene in the solvent. The selectivity is calculated as separation factors as defined above. The feed mixture was further diluted while contacted with 2 gr. of pre-wetted zeolite in 10 ml of the diluent of interest. As indicated the diluent type affects in this case the separation and decalin was not found to have the same effect as mesitylene. This shows that adsorptive distillation may also be applied in separation of aromatic compounds, particularly the separation of benzene from toluene in hydrocarbon mixtures.

Example 7

Another test was performed in which a $C_7$ isomerate was passed first over an adsorptive distillation 90 cm column as applied in the previous experiments filled with zeolite 5A and operated at the same conditions. The process was performed in the recycle mode as mentioned in Example 4. The distillate from the 5A column, now with a very low concentration of n-heptane, was then fed to a similar adsorptive distillation column filled with ZSM-5 Si/Al 400 zeolite in bead form and operated at 150° C. This allowed us to target the removal of 2-methylhexane (2 MH) and 3-methylhexane (3 MH), which were specifically retained in the ZSM-5 zeolite. The distillate from this had approximately 10% of the original methylhexanes left. The composition is given in FIG. 5. These experiments show that separate streams of higher concentrations of specific isomers can be obtained by the adsorptive distillation approach with high recovery in the distillate. Both beds had been regenerated using n-pentane and the desorbent was co-produced during the distillation apparently without affecting the specificity of the adsorbent. Compound abbreviations are as given in the literature and are placed in order of increasing boiling point. Moreover, the inventive process enables that the compound 2,3 dimethylpentane (23DMP) having a relatively high RON of 91 be found in the final distillate instead of being separated together with the methylhexanes, as it is the case when conducting conventional distillation due to the very similar boiling points of 23DMP and methylhexanes.

What is claimed is:

1. A process for the separation of benzene from other hydrocarbons in a hydrocarbon mixture, the process comprising:
   (a) combining said hydrocarbon mixture with a diluent liquid solution having a boiling point which is higher than that of the hydrocarbon mixture, and passing said hydrocarbon mixture combined with said diluent liquid solution to a distillation column of a distillation stage, said distillation column comprising an adsorption zone packed with a solid adsorbent which is in contact with the diluent liquid solution;
   (b) withdrawing from said distillation stage a distillate stream containing other hydrocarbons than benzene and retaining benzene in the adsorption zone, wherein said adsorption zone contains zeolite X, zeolite Y, or mixtures of both; and
   (c) withdrawing from said distillation stage a stream containing said diluent liquid solution and subsequently returning said stream directly back to the distillation column of step (a).

2. A process according to claim 1, wherein step (a) comprises the steps of combining a first stream containing said hydrocarbon mixture with a second stream of said diluent liquid solution having a boiling point which is higher than that of the hydrocarbon mixture and passing the combined stream to said distillation stage.

3. A process according to claim 1, wherein the diluent liquid solution is a solution of compounds selected from the group consisting of benzene substituted with 1, or 3 to 6 methyl, ethyl or propyl groups and mixtures thereof.

4. A process according to claim 1, further comprising desorbing the adsorbed benzene from the adsorption zone by passing a desorbent stream through said adsorption zone and withdrawing a stream containing benzene, wherein the desorbent is a hydrocarbon containing at least 50 wt % cyclohexane.

* * * * *